(12) United States Patent
Lehmann

(10) Patent No.: US 6,561,800 B2
(45) Date of Patent: *May 13, 2003

(54) TOOTH SHADE ANALYZER SYSTEM AND METHODS

(75) Inventor: Maryann Lehmann, Darien, CT (US)

(73) Assignee: Shade Analyzing Technologies, Inc., Darien, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/057,663

(22) Filed: Jan. 25, 2002

(65) Prior Publication Data

US 2002/0064751 A1 May 30, 2002

Related U.S. Application Data

(63) Continuation of application No. 09/918,147, filed on Jul. 30, 2001, which is a continuation of application No. 09/688,542, filed on Oct. 16, 2000, now Pat. No. 6,305,933, which is a continuation of application No. 09/385,615, filed on Aug. 30, 1999, now Pat. No. 6,132,210, which is a continuation of application No. 09/082,030, filed on May 20, 1998, now Pat. No. 5,961,324, which is a continuation-in-part of application No. 08/494,979, filed on Jun. 26, 1995, now Pat. No. 5,766,006.

(51) Int. Cl.$^7$ ............................................. A61C 19/10
(52) U.S. Cl. ......................................... 433/26; 356/408
(58) Field of Search ........................ 433/26, 29, 203.1, 433/215; 356/402, 405, 406, 408

(56) References Cited

U.S. PATENT DOCUMENTS

| | | | | |
|---|---|---|---|---|
| 5,012,431 A | * | 4/1991 | Stanziola | 382/162 |
| 5,177,694 A | | 1/1993 | Graham et al. | 364/526 |
| 5,231,472 A | * | 7/1993 | Marcus et al. | 356/402 |
| 5,313,267 A | * | 5/1994 | MacFarlane et al. | 356/405 |
| 6,132,210 A | * | 10/2000 | Lehmann | 433/26 |
| 6,305,933 B1 | * | 10/2001 | Lehmann | 433/26 |
| 6,358,047 B2 | * | 3/2002 | Lehmann | 433/26 |

* cited by examiner

Primary Examiner—Pedro Philogene
(74) Attorney, Agent, or Firm—Winston & Strawn

(57) ABSTRACT

A method for determining a patient's tooth shade, by generating an electronic image of a patient's tooth wherein the image includes color information representative of the patient's tooth shade; storing color information representative of a plurality of tooth shades; and comparing the color information of the image with the stored tooth shade color information to identify one or more tooth shades having a combined color that corresponds to the patient's tooth shade. the image of the patient's tooth and the stored tooth shade color information are electronically displayed in color to enable a viewer to comparatively determine the color of the patient's tooth shade. Preferably, the patient's tooth shade is determined by selecting portions of the electronically displayed image of the tooth; determining the color of the selected portions; and comparing that color information with the stored tooth shade color information to determine the color of that portion of the patient's tooth. The selection of portions of the tooth is generally repeated until a tooth shade color is determined for all spatial locations of the image of the patient's tooth.

19 Claims, 10 Drawing Sheets

TOOTH SHADE ANALYZER SYSTEM AND METHODS

CROSS-REFERENCE TO RELATED APPLICATIONS

This application is a continuation of application Ser. No. 09/918,147 filed Jul. 30, 2001, which is a continuation of application Ser. No. 09/688,542 filed Oct. 16, 2000, now U.S. Pat. No. 6,305,933, which is application is a continuation of application Ser. No. 09/385,615 filed Aug. 30, 1999, now U.S. Pat. No. 6,132,210, which application is a continuation of application Ser. No. 09/082,030 filed May 20, 1998, now U.S. Pat. No. 5,961,324, which application is a continuation-in-part of application Ser. No. 08/494,979 filed Jun. 26, 1995, now U.S. Pat. No. 5,766,006.

BACKGROUND ART

In dentistry, there has been a shift in recent years from a philosophy of drilling and filling to one of prevention and cosmetics. By way of example, many people today are choosing to have clinical procedures done to enhance their smile and appearance. Most of these procedures involve the modification of tooth shape, alignment, and/or color.

The use of intraoral video and/or imaging systems (hereinafter "intraoral camera system") has grown rapidly in dentistry over the past few years. Such systems are widely utilized in "show and tell" settings, i.e., where the dentist can show and illustrate particular features of a patient's mouth. These intraoral camera systems are rapidly becoming key complex diagnostic and treatment planning. Presently, approximately 30% of the practicing dentists in the age group between about 35–54 own and utilize intraoral camera systems. It is expected that that percentage will only increase with increased familiarity. See *Dental Procedures Report*, pgs. 22–24, February 1995.

A necessary step in altering a patient's tooth color is to determine the "shade" of the existing tooth. For example, those persons seeking a whiter, brighter smile are still assessed to establish their existing tooth color so that an appropriate before and after comparison can be made. Shade determination is even more important for those persons seeking reconstructive work, since one goal of the reconstructive process is to achieve a natural appearance. Therefore, it is important to know the existing tooth shade so that it can be accurately matched with the new restoration.

The dental profession utilizes standardized shade guides created by those companies which manufacture the reconstructive materials. One well-known shade guide is the Vita™ shade guide, which includes sixteen different shades. Other, less popular shade guides include those guides provided by Bioform™ and SR-Vivadent™.

These shade guides are utilized in a rudimentary fashion. The guide itself is a plastic plate with a plurality of removable color tabs that are shaped like a tooth, e.g., the front tooth. Typically, to assess a patient's tooth shade, a dentist removes one of the colored tabs and holds it up to the patient's tooth so that she can "eyeball" the closest match possible. Understandably, there are many variables to this method, some of which stem from the subjectivity of the dentist making the eyeball assessment.

Once the tooth shade is determined, the information is used relative to the particular procedure needed. In bonding or filling a tooth, for example, the composite materials required for the restoration are specified within the range of the shade guide, e.g., one of sixteen shades for the Vita™ range. More particularly, if a crown, bridge or denture is needed, the patient's shade must be determined and communicated correctly to the lab that make the crown, bridge or denture.

The communication of shade information between the dentist and the lab is extremely important. Often, there is a break-down or failure in this communication, resulting in a poor shade match for the patient. In some cases, a particular dentist utilizes an uncommon shade guide, thereby leaving the lab technician to eyeball and convert the shade information to a Vita standard shade (since porcelain is often made from the Vita™ shade guide). This too can result in improper shade matching.

The process for selecting the porcelain for a particular tooth shade illustrates the difficulty in assessing and manufacturing the correct color match. If, for example, a crown of Vita™ shade A3 is desired, porcelain is built by hand with a paint brush onto a model of the tooth to be restored. The porcelain is built in layers on the model to achieve translucency and natural appearance. Each layer has a particular color and intensity associated with it. To generate shade A3, the technician follows a "recipe" that is given by the manufacturer Vident™, requiring a different shade for each layer of porcelain applied. If a doctor asks for a shade that is not a Vita™ standard shade, the technician typically seeks to achieve that shade by combining different porcelain shade combinations together, to increase or decrease the chroma, hue and value of the shade.

To further complicate the color-matching process, some dentists are simply not skilled in taking and determining shade information. Therefore, these dentists sometimes send their patients directly to the lab where the technician can determine the shade information. Alternatively, these dentists sometimes have a technician come to their office. In either event, there is, at times, one more level of subjective uncertainty injected into the correct match and determination of a patient's tooth shade. Thus, there is a need for more improvements in this area.

SUMMARY OF THE INVENTION

The invention relates to a method for determining a patient's tooth shade comprising the steps of electronically imaging a patient's tooth to obtain an image which includes color information representative of tooth color; determining the patient's tooth color from the color information of the image; and displaying the determined tooth color to identify one or more tooth shades having a combined color corresponding to the determined tooth color.

Preferably, the displayed data includes RGB chromaticities of the color image, and the patient's tooth color is determined by averaging the color information at selected locations of the image which correspond to different spatial locations of the patient's tooth. If desired, the color information of the patient's tooth can be electronically stored for use at a later time.

The identification of tooth shade(s) is generally made by comparing the determined tooth color to a plurality of electronically stored tooth shades. If desired, both the identified tooth shade(s) and the color information of the image of the patient's tooth can be electronically displayed to enable a visual comparison to be made therebetween. Preferably, information which includes the identified tooth shade(s) can be communicated to a laboratory for use in manufacturing a reconstructed tooth for the patient. This is typically done by painting one or more porcelain layers onto a model of the patient's tooth, each of the layers of porcelain corresponding to the identified tooth shade(s) or a color fraction thereof.

For optimum results, either the patient's tooth or a tooth shade is imaged at a controlled, reproducible distance, and a reference color to assist in determining the patient's tooth color from the color information of the image. Also, the patient's teeth are cosmetically whitened before conducting the electronic imaging step.

Another aspect of the present invention relates to a method for determining a patient's tooth shade comprising the steps of electronically imaging a patient's tooth to obtain an image which includes color information representative of tooth color; determining the patient's tooth color from the color information of the image; and identifying one or more tooth shades having a combined color corresponding to the determined tooth color. The patient's tooth color can be determined by electronically displaying the color information of the image and by averaging the color information at selected locations of the image which correspond to different spatial locations of the patient's tooth.

The method may include the further step printing the electronically displayed color information of the image to produce a record or electronically storing the color information of the patient's tooth for use at a later time. Advantageously, the identification of tooth shade(s) is made by comparing the determined tooth color to a plurality of electronically stored tooth shades, and both the identified tooth shade(s) and the color information of the image of the patient's tooth can be electronically displayed to enable a visual comparison to be made therebetween. Information regarding the identified tooth shade(s) can be communicated to a laboratory for use in manufacturing a reconstructed tooth for the patient. The reconstruction is performed by painting one or more porcelain layers onto a model of the patient's tooth, each of the layers of porcelain corresponding to the identified tooth shade(s) or a color fraction thereof.

In order to optimize the color determining step, one of the patient's tooth or a tooth shade or both can be imaged at a controlled, reproducible distance. The step of isolating the patient's tooth from stray light can be used to enhance the image. Also, a reference color can be provided to assist in determining the patient's tooth color from the color information of the image. When used, it is helpful to surround the patient's tooth with the reference color before the imaging step. Often, the patient's tooth is cosmetically whitened before conducting the electronic imaging step.

The invention also relates to a system for determining the tooth shade of a patient's tooth, comprising a camera for capturing an image of the patient's tooth, the image including color information representative of tooth color; and a shade analyzer sub-system which electrically communicates with the camera. The shade analyzer typically includes a color processor for determining the color of the patient's tooth from the color information of the image; and a color correlation section for evaluating the color of the patient's tooth and for identifying a tooth shade having a color corresponding to the color of the patient's tooth. Preferably, the system further comprises an electronic storage medium for storing shade information representative of a plurality of tooth shades, each tooth shade corresponding to a different tooth color.

The camera is preferably a color CCD camera comprising an array including a plurality of proximately located pixels. Generally, the camera comprises three CCD arrays, each of the arrays collecting image data corresponding to red, green or blue, and the subsystem further comprises a section for integrating at least a portion of the tooth to determine an average color over that portion of the tooth by combining color fractions of known tooth shades. Thus, the color correlation section should include sufficient memory for associating the color of the patient's tooth with one or more known tooth shades.

Advantageously, the system further comprises a monitor for simultaneously displaying color information of the tooth and tooth shade information so that visual comparisons can be made. Also, a printer can be used for printing the color information displayed on the monitor for communicating this information to a laboratory for reconstruction of the patient's tooth.

The color processor preferably includes electronic circuitry which determines RGB chromaticities of the color image, each of the plurality of tooth shades has a corresponding RBG representation of the tooth color, and the electronic circuitry quantitatively compares the RGB chromaticities with the RGB representation of each of the tooth shades, thus comparing or identifying a tooth shade based upon a comparison of the chromaticities and the RGB representations. For optimum results, the system further comprises a sample box (or isolation sleeve) for isolating the tooth from stray light. This isolation sleeve preferably includes a first compartment that contains a reference color and a second compartment for receiving the patient's tooth or a reference shade. It also may have a side wall of a length which assists in obtaining reproducible results by positioning the camera at a controlled distance from the patient's tooth or the tooth shade. Even without the isolation sleeve, the system may include a reference card having a background color to enhance the image of the patient's tooth, the card optionally including an opening for receiving the patient's tooth or a reference shade.

BRIEF DESCRIPTION OF THE DRAWINGS

A more complete understanding of the invention may be obtained by reference to the drawings, which illustrate preferred embodiments in which.

DETAILED DESCRIPTION OF THE PREFERRED EMBODIMENTS

Figure 1:
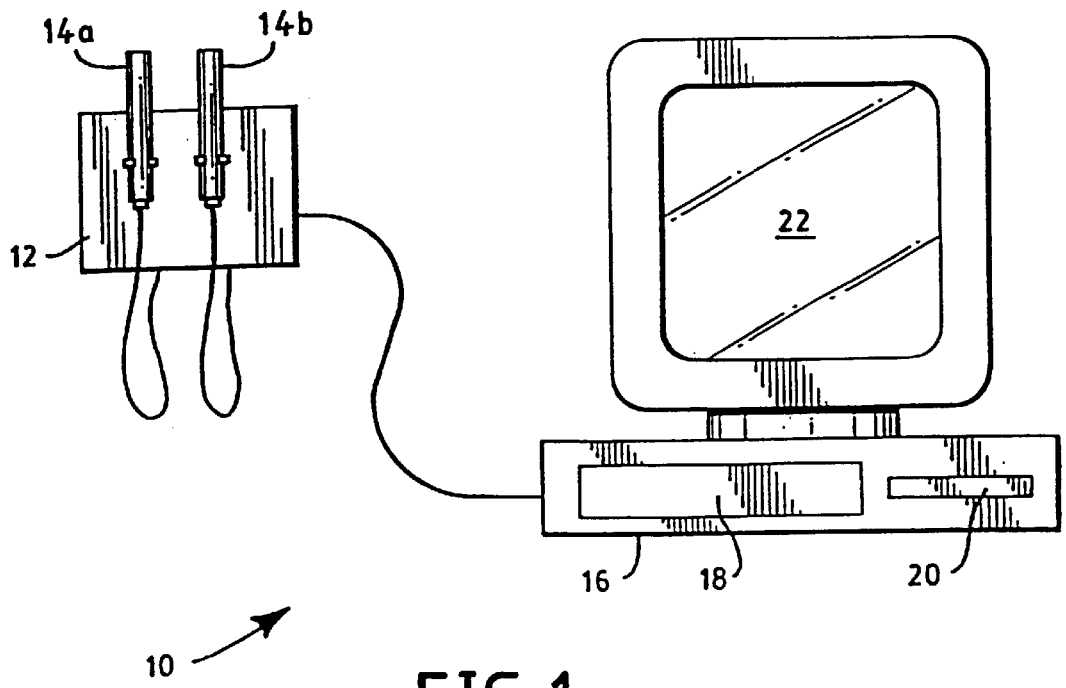
FIG. 1 shows a prior art intraoral camera system.

A number of different aspects of the invention are disclosed. In one aspect, the invention provides a system for determining the tooth shade of a patient's tooth. A camera, preferably an intraoral camera, captures the image of the patient's tooth, including color information representative of the tooth's color. A shade analyzer sub-system is in electrical communication with the intraoral camera, and preferably has (i) a color processing section for determining the color of the patient's tooth from the color information of the image; (ii) storage memory for storing shade information representative of a plurality of tooth shades (i.e., each of the tooth shades corresponds to a different tooth color), (iii) a color correlation section for comparing the color of the patient's tooth to the plurality of tooth shades and for identifying a tooth shade with a color corresponding to the color of the patient's tooth, and (iv) means such as a display terminal for communicating the identified tooth shade to a user of the system.

In another aspect, the system includes a monitor used to display the color image to a user of the system. The shade analyzer sub-system thus communicates a tooth color representative of the identified tooth shade to the monitor, thereby providing a user of the system with a visual comparison of the patient's tooth color with the color of the identified tooth shade.

In a further aspect, the color processing section determines RGB chromaticities of the color image, and each of the plurality of tooth shades has a corresponding RGB representation of the tooth color stored in memory. In such an aspect, the color correlation section quantitatively compares the RGB chromaticities with the RGB representation of each of the tooth shades, and compares and identifies a tooth shade based upon an comparison of the chromaticities and the RGB representations.

In still another aspect of the invention, the system associates one or more of the plurality of tooth shades with at least one standardized shade corresponding to a particular manufacturer's porcelain product. Accordingly, the system communicates the standardized shade to a user of the system so that the desired tooth may be constructed.

The color correlation section of the invention can also identify a combination of tooth shades having a combined color corresponding to the color of the patient's tooth. As such, the system can (i) associate each of the tooth shades in the combination with at least one standardized shade corresponding to an particular manufacturer's porcelain product, (ii) specify fractions of each of the standardized shades needed to form the combined color, and (iii) communicate information identifying the fractions of each of the tooth shades in the combination to a user of the system.

The invention also provides a tooth shade analyzer system for determining the tooth shade of a patient's tooth. One section of the analyzer communicates with an intraoral camera of the type which captures the image of the patient's tooth, including color information representative of a color of the tooth. Other sections of the analyzer (i) determine the color of the patient's tooth from the color information of the image, and/or (ii) store shade information representative of a plurality of tooth shades. A color correlation section compares the color of the patient's tooth to the plurality of tooth shades and identifies one or more tooth shades with a combined corresponding to the color of the patient's tooth. Finally, the system includes means for communicating with devices such as the display monitors to communicate the one or more identified tooth shades to a user of the system. In this manner, the analyzer matches the patient's tooth with one or more corresponding tooth shades and assists in reconstructing the patient's tooth.

The invention also includes a method for determining the tooth shade of a patient's tooth, including the step of: capturing an image of the patient's tooth with a camera, the image including color information representative of tooth color; determining the color of the patient's tooth from the color information of the image; comparing the color of the patient's tooth to a plurality of tooth shades, the tooth shades being stored in an electronic medium; identifying one or more tooth shades with a combined color corresponding to the color of a patient's tooth; and communicating the one or more identified tooth shades to a user of the system.

A further method of the invention compares to tooth shade of a patient's tooth after the patient's teeth are cosmetically whitened, including the steps of: capturing a first image of the patient's tooth with an intraoral camera before the tooth is cosmetically whitened, the first image including first color information representative of a color of the tooth; processing the color information of the image to determine the color of the patient's tooth; comparing the color of the patient's tooth to a plurality of tooth shades, the tooth shades being stored in an electronic medium; identifying one or more tooth shades with a combined color corresponding to the color of the patient's tooth; whitening the teeth; communicating the one or more identified tooth shades to a user of the system; and viewing the patient's tooth on a monitor after the whitening step while simultaneously displaying an image of the patient's pre-whitened tooth, to provide before and after imagery.

In another aspect of the invention, a process is provided for manufacturing a reconstructive tooth for a patient, including the step of: capturing the image of the patient's tooth with an intraoral camera, the image including color information representative of a color of the tooth; processing the color information of the image to determine the color of the patient's tooth; comparing the color of the patient's tooth to a plurality of tooth shades, the tooth shades being stored in an electronic medium; specifying one or more tooth shades, and any fractions thereof, having a combined color corresponding to the color of the patient's tooth; and painting one or more layers of porcelain onto a model of the patient's tooth, each of the layers of porcelain corresponding to the specified tooth shades and the fractions thereof.

The invention also includes a system for determining the tooth shade of a patient's tooth by utilizing color CCD cameras. In one aspect, a color CCD camera captures the image of the patient's tooth, including color information representative of a color of the tooth. A shade analyzer sub-system is connected for electrical communication with the CCD camera, and has (i) a color processing section for determining the color of the patient's tooth from the color information of the image, (ii) a storage section for storing shade information representative of a plurality of tooth shades, each of the tooth shades corresponding to a different tooth color, (iii) a color correlation section for comparing the color of the patient's tooth to the plurality of tooth shades and for identifying a tooth shade with a color corresponding to the color of the patient's tooth, and (iv) a section for communicating the identified tooth shade to a user of the system.

In accord with the invention, the CCD camera can include three CCD arrays, each of the arrays collecting image data corresponding to a color selected from the group of red, green and blue. Alternatively, the CCD camera can include a single CCD array, including a plurality of proximately located pixels corresponding to a color selected from the group of red, green and blue, each of any group of three pixels having a different color associated therewith.

FIG. 1 illustrates a typical prior art intraoral camera system 10. The system 10 includes a wall-mounted intraoral camera 12, which includes twin halogen lamp light source (not shown) for uniform illuminance, one or more handpieces 14a, 14b, a digital video processor 16 (typically an IBM-compatible PC), which includes a hard drive 18 and floppy drive 20, and a color video monitor 22.

In operation, a dentist points a selected handpiece 14a, 14b at the target location within the patient's mouth to illuminate and view the resulting, full color image on the screen of a monitor 22. The endoscope handpieces 14a, 14b come in varying styles, including a wide angle configuration, e.g., a 100 degree field of view (FOV) for posterior and anterior views, and a near 0 degree FOV for a full-arch and full face images. The processor 16 provides storage for any selected image, and can further display selected close-ups on the monitor screen 22 through zoom capabilities.

There are several manufacturers of intraoral camera systems, offering an array of features. For example, Insight™, of San Carlos, Calif., offers a Power 0/100 similar to the one shown in FIG. 1. Other manufacturers include Cygnus Instruments, Inc. (Cygnascope™), of Goleta, Calif. VistaCam™ is yet another prior art intraoral camera system that incorporates a 90-degree FOV fiberoptic handpiece that delivers full color images from about 6 mm, i.e., the size of one typical tooth, to an image of the patient's whole smile. Therefore, the intraoral camera systems described above offer full color imagery of a patient's tooth. The image may be stored, e.g., in a personal computer on a disk 18, 20. Also, the images can be advantageously displayed on the monitor screen 22.

Figure 2:
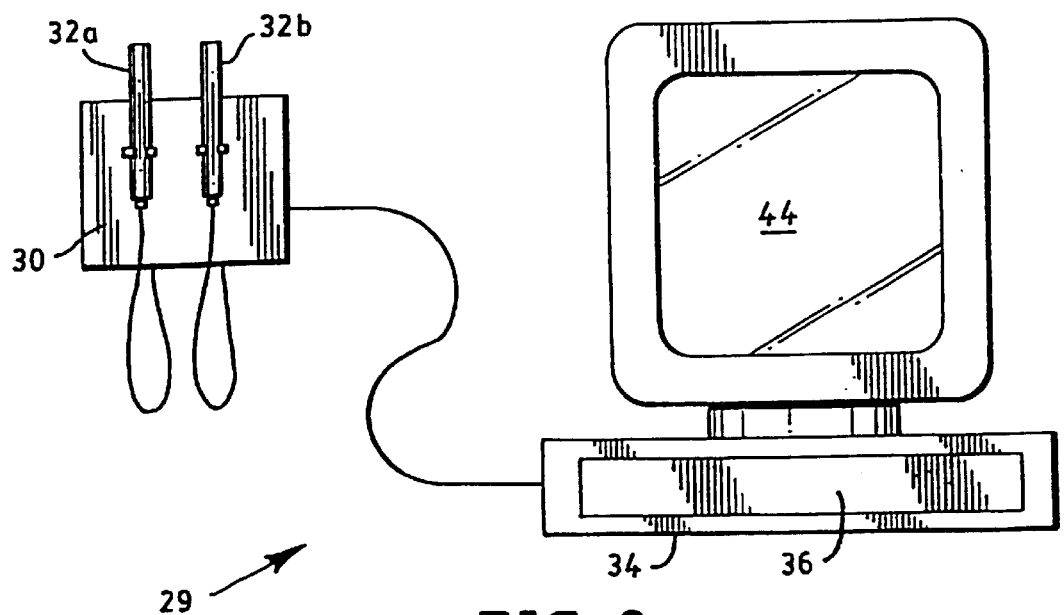
FIG. 2 illustrates a tooth shade analyzer system constructed according to the invention.

The invention makes use of an intraoral camera system of the type described above. Specifically, FIG. 2 illustrates one embodiment of the invention and which shows a tooth shade analyzer 29 including an intraoral camera 30, associated handpieces 32a, 32b, and a shade-analyzer subsystem 34. Preferably, the subsystem 34 is a digital video processor that is similar to the processor 16 of FIG. 1, and thus preferably includes the video processing capabilities of the processor 16, such as known to those skilled in the art. A storage medium 36, such as a hard disk 18 or floppy 20, stores digital color images of a plurality of tooth shades, such as each of the sixteen shades of the Vita™ shade guide. The storage medium 36 further stores any images collected by a user of the system 29.

Figure 3:
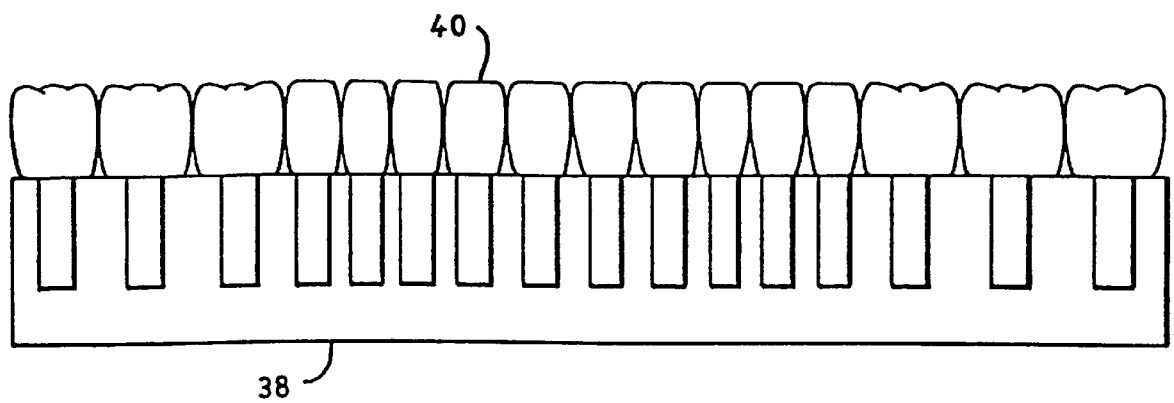
FIG. 3 illustrates a typical prior art tooth shade guide.
Figure 3A:
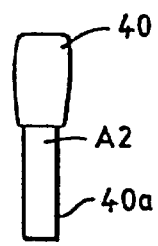
FIG. 3A illustrates one tooth shade tab of the shade guide in FIG. 3.

The storage of the digital color images of one or more shade guides is relatively straight-forward. In particular, FIG. 3 illustrates one shade guide 38 having sixteen separate tabs 40. Each of the tabs 40 is removable from the guide 38 so that it can be placed and viewed next to the patient's teeth. FIG. 3A illustrates one tab 40 that is removed from the guide 38. The tab holder 40a typically includes color information about the selected tab 40, here shown as shade "A2."

Figure 4:
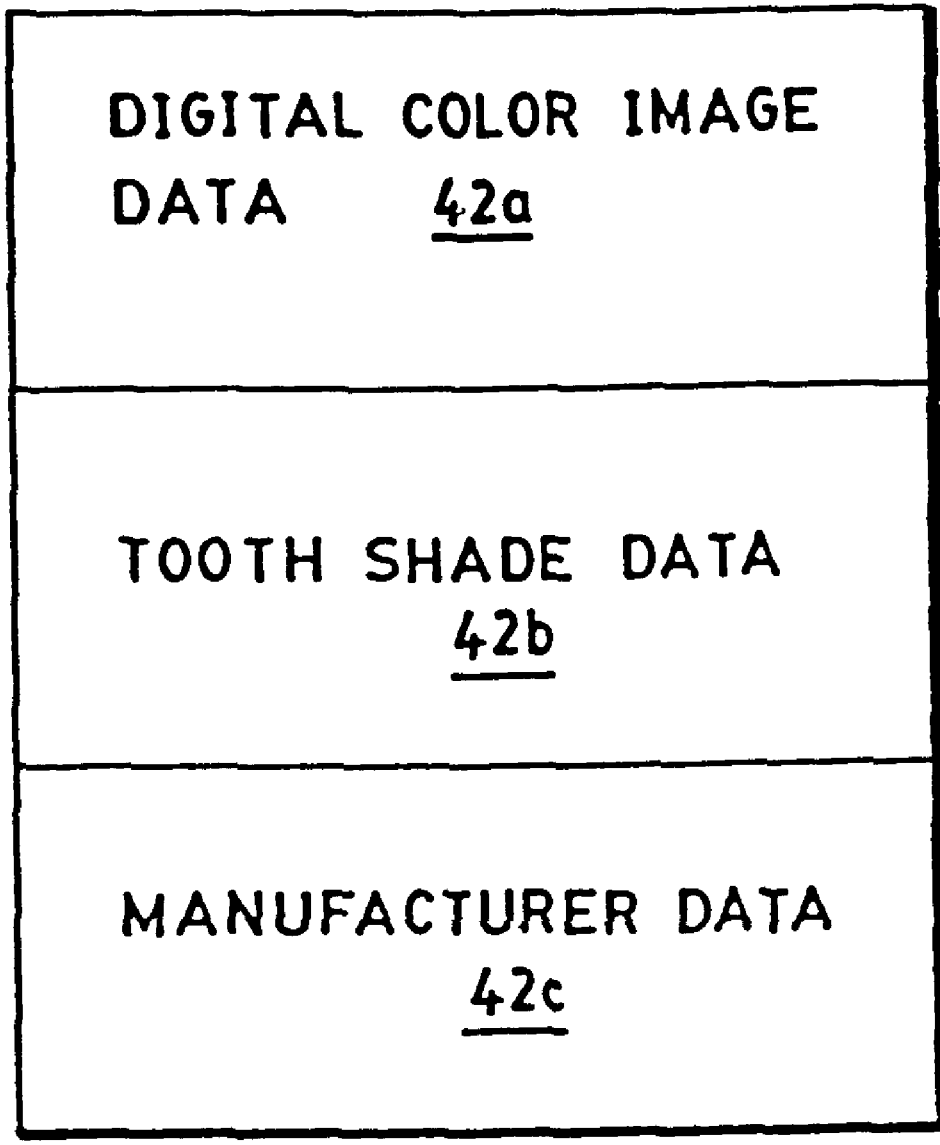
FIG. 4 illustrates a digital data block constructed according to the invention for specifying a tooth shade color, color image information, and an associated manufacturer.

In accordance with the invention, each of the tabs 40 are illuminated by one or the handpieces 32a or 32b so that a color image is captured and stored in the medium 36. The image is accompanied by associated information about that shade, such as the manufacturer type, e.g., the Vita shade guide, and the particular shade, e.g., "A2." For example, FIG. 4 illustrates one storage block 42 of data for storage as digital memory and which is representative of one tooth shade. In particular, block 42a includes digital color image information, block 42b denotes the particular tooth shade, e.g., "A2," and block 42c denotes the manufacturer name, so that the associated tooth shade porcelain can be purchased from the correct manufacturer. Generally, the blocks 42b, 42c of data are represented by digital words that specify the information, while block 42a includes image data corresponding to both color and spatial information.

Preferably, the color image data within the block 42a is in a RGB format (i.e., Red, Green, Blue digital format, such as known to those skilled in the art) which specifies a color pixel within the image to an accuracy exceeding the number and color spread of the selected shade guides. For example, if sixteen shades are stored within the memory 36, then the bit-specificity required of the color-coded data within the image block 42a should span and discriminate at least those sixteen shades of white. For example, if each color of the RGB is specified at 3-bits each, then 256 standard colors are discernible by the system 29 to cover sixteen tooth shades. Greater color determination accuracy is achieved with increased color-coding. In addition, if all the manufacturers of tooth shades are loaded into the memory 36, then even more color-coded accuracy is required, e.g., 8-bit per RGB color.

The display of the color imagery within the digital data block 42a is known to those skilled in the art. Specifically, the RGB information within the data block 42a specifies the color for each pixel on the monitor 44, FIG. 2, which is similar in capability to the monitor 22 of FIG. 1. The particular video driver (not shown) used to drive the monitor 44 specifies and controls the color and image display as appropriate. The RGB format specifies a color corresponding to signals which produce a suitable color picture on the monitor having the reference colors defined by the RGB chromaticities.

Figure 5:
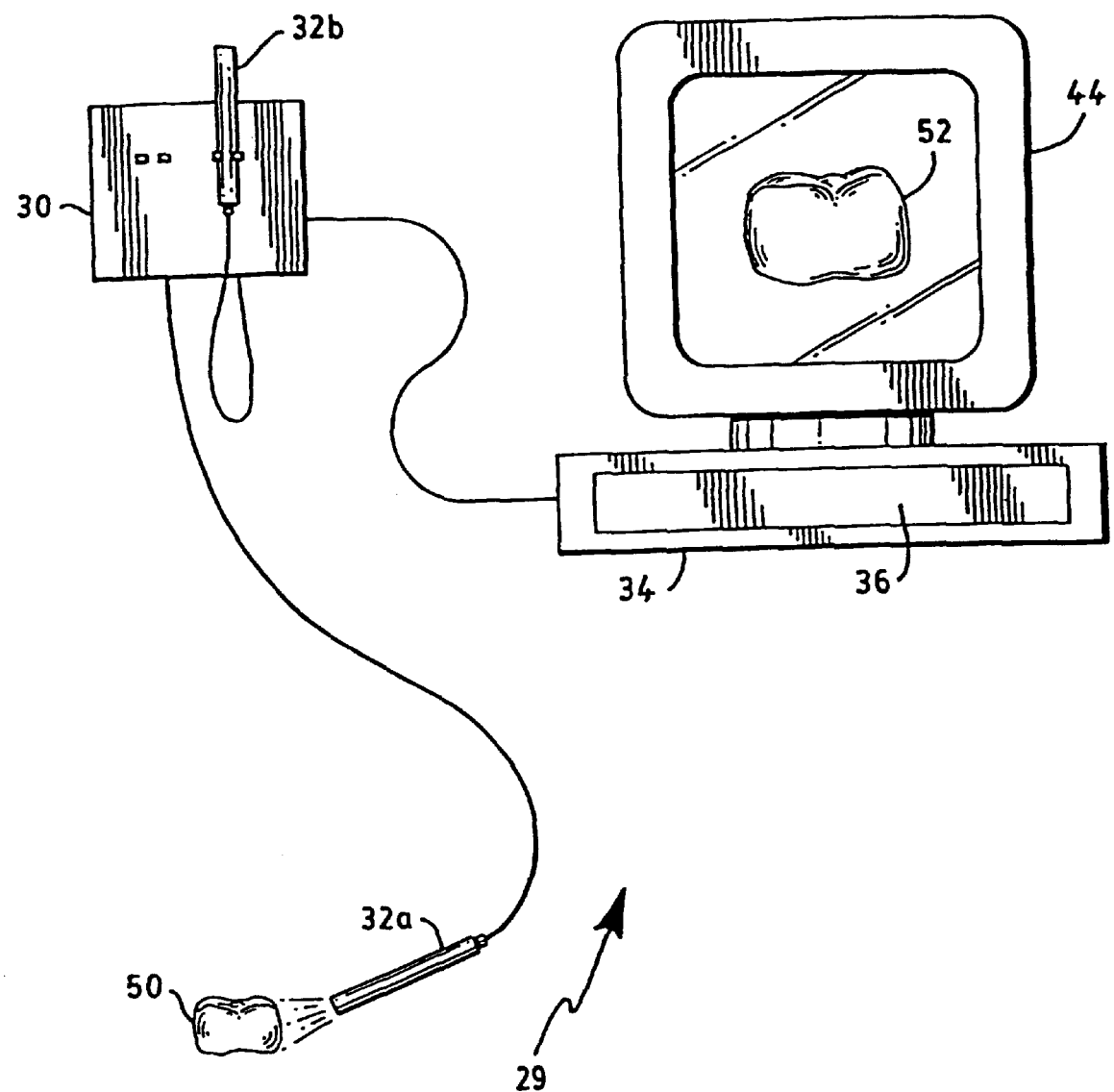
FIG. 5 shows an operational use of the system of FIG. 2.

Once the plurality of shades are loaded into memory 36, the system 29 is ready for use. FIG. 5 illustrates this process in more detail. A user illuminates the desired tooth 50, (illustratively shown outside of the patient's mouth) with the handpiece 32a such that an image 52 of the tooth 50 is displayed on the monitor 44. Although this step of forming an image on the screen 44 is not required, it helps to assess the accuracy to which the camera 30 captured the image 52.

As above, this image data 52 is stored into a block such as block 42, FIG. 4. The shade analyzer-subsystem then compares the digital information within the block of data representing the image 52 with the blocks of data representative of the several tooth shades. In one embodiment, a comparison of the RGB values is made between the tooth image data 52 and the several shades to find a best fit or match.

It is important to note that this process has several advantages over the prior art. In particular, as long as the same camera 30 captures the data of the tooth shades and the patient's tooth shade data, it does not matter that the stored image color within the processor 34 match the perceived color or hue observed by a typical human. That is, as long as the data captured by the system 29 correlates to the same reference, e.g., the same camera 30, the match between the image 52 and the plurality of tooth shades will be calibrated automatically. This is in contrast to many of the prior art references, e.g., U.S. Pat. No. 5,383,020, which requires a sensitivity maxima of the human eye. The invention has no corresponding limitation because the camera of the system 29 objectively gathers the data from the same internal source. Nevertheless, it is preferable that the color display and coding of the camera 30 correspond to natural and perceived colors so that the image appears normal to a viewer.

Those skilled in the art should appreciate that the data from the plurality of tooth shades can also be loaded from a floppy disk into the subsystem 34. More particularly, the tooth shade data from the one or more manufacturers can be installed directly into the system 29 without physically capturing the image of each tooth shade, provided that the data is captured by a camera that is similar to the camera 30, or by a camera that is calibrated to within an acceptable margin to the camera 30. In this manner, a user of the system 29, e.g., a dentist, need never have actual tooth shade tabs at the office. Rather, the system 29 is used to capture color data on the patient's tooth; and the stored tooth shade information within the system 29 is automatically extracted, including a manufacturer identifier.

Figure 6:
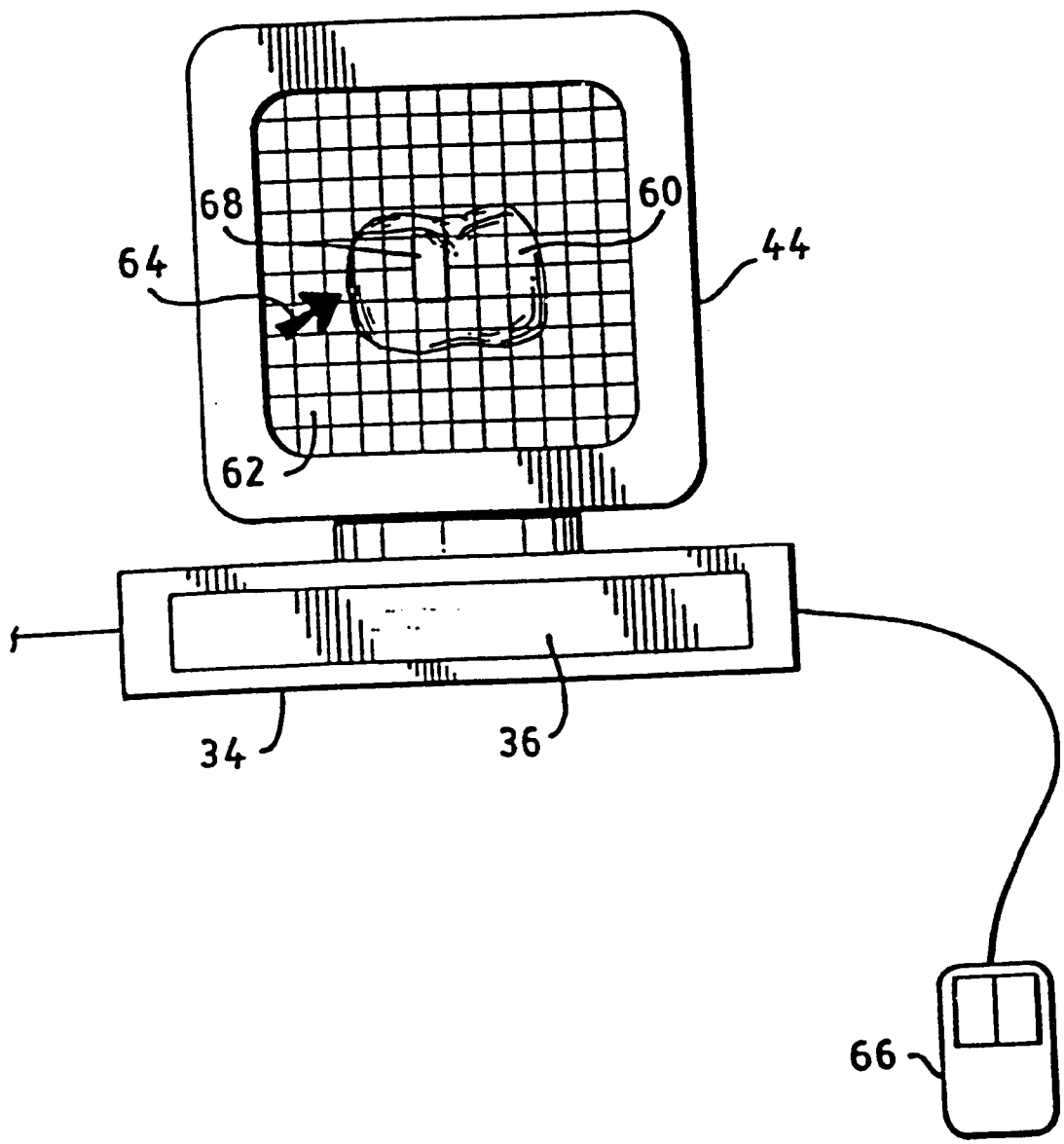
FIG. 6 illustrates image averaging and specification techniques, according to the invention.

It is worth noting that not all tooth shade information is readily derived from the patient. In particular, unlike the tooth shades from the shade guides, which are very uniform in color, a patient's tooth can include a myriad of different shades. Tooth stains and the like alter the tooth's color spatially, so that a selection or integration of color is preferred. FIG. 6 illustrates one embodiment of the invention for dealing with this non-uniformity.

Specifically, FIG. 6 shows a tooth image 60 of a patient's tooth on the monitor 44. Each pixel 62, which is grossly over-sized for illustrative purposes, corresponds to a different spatial location and color of the tooth's image 60. Accordingly, a user of the system 29 can select one of the pixels at the desires color by pointing and clicking a mouse pointer 64, via the mouse 66, at any selected location (the details of the mouse and mouse pointer are widely known to those skilled in the art without further reference hereto, and are shown for illustrative purposes only). This selected information is then stored with the block of data, e.g., block 42b of FIG. 4.

Alternatively, the image of the tooth 60 can be averaged over a selected area by selecting a particular region for which the color imagery is averaged. For example, if the tooth 60 is to be averaged over the two pixels identified by the outline 68, then the subsystem 29 averages the two RGB values and specifies the tooth shade match in block 42b as an average of the two.

Figure 7:
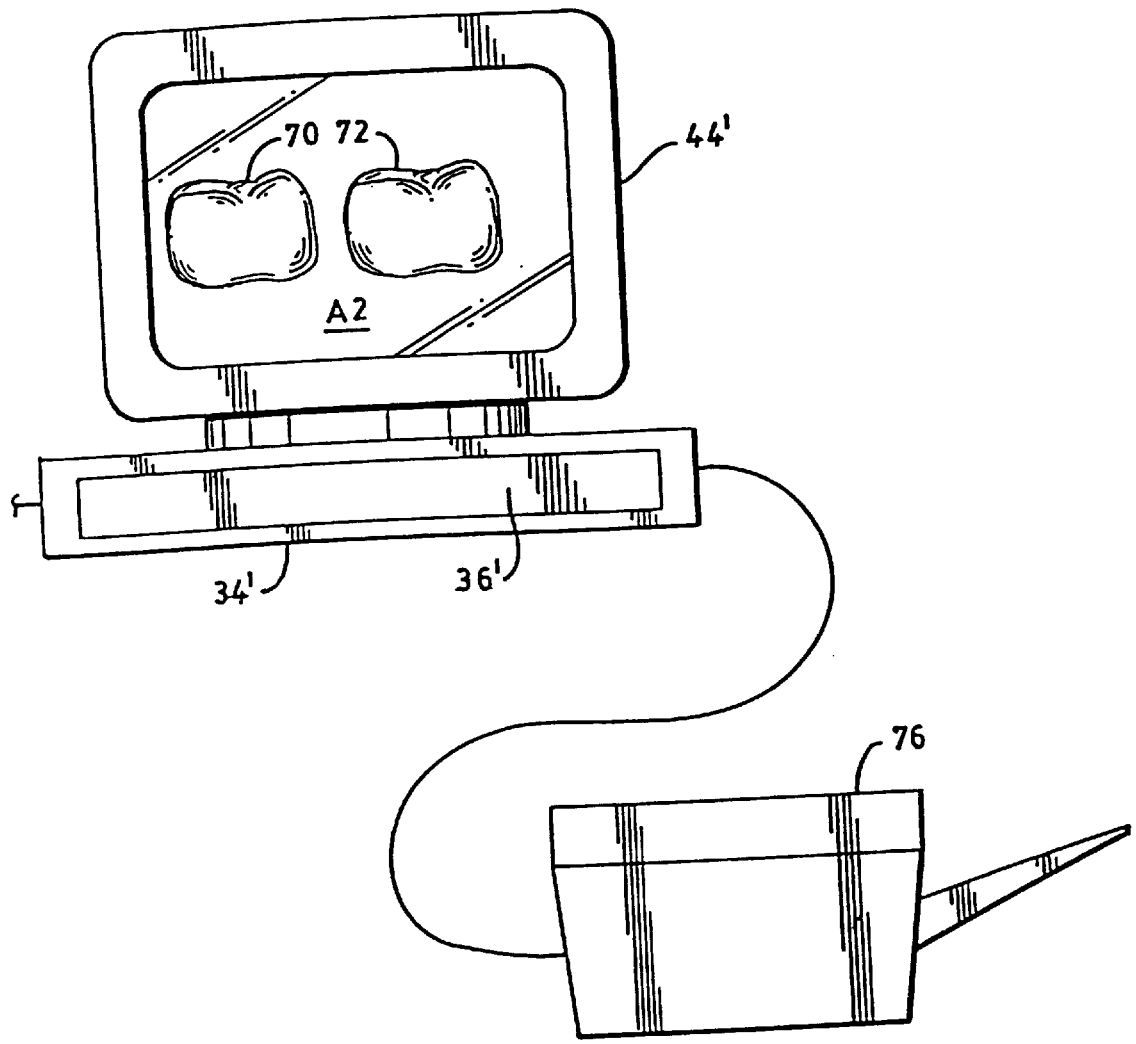
FIG. 7 illustrates an image comparison on the system of FIG. 2.

FIG. 7 illustrates another monitor 44' and subsystem 34' constructed according to the invention, each of which is similar to the monitor 44 and subsystem 34 of FIG. 2, respectively. In the illustrated embodiment, an image 70 of a patient's tooth is matched to the appropriate shade, as above, and then an image 72 of the matched shade is also displayed on the monitor 44'. The subsystem 34' further generates and displays the tooth shade identifying match, e.g., "A2," on the screen 44' so that the ordering information about the tooth reconstruction is easily ascertained. In the illustrated embodiment, a visual comparison between the tooth and the selected shade is made available to both the dentist and the patient. The display 44' can also display the particular porcelain product information.

If should be apparent to those skilled in the art that the data and information displayed on the monitor 44' can also be downloaded to a printer 76, so that a permanent record of the exam is obtained in hard-copy form.

In the event that the system 29 of FIG. 2 does not find a close match to one existing tooth shade, the subsystem 34 specifies a combination of tooth shades that correspond to the color of the patient's tooth image data, e.g., the image 52 of FIG. 5. Preferably, this information is determined in fractions of the appropriate shade, e.g., ½ "A2" and ½ "C4." Such fractions are determinable, according to one embodiment of the invention, by comparing the RGB data within the plurality of tooth shade blocks 42b with the actual patient's tooth shade image information. If the RGB data of the patient's tooth is equal to the chromaticity sum of ½ "A2" and ½ "C4," then such a fraction is entered into the match data block 42b for the selected tooth shade, and displayed on the screen 44 for the user. The chromaticity mathematics used to combine and subtract colors is known to those skilled in the art. Further detail may be found with reference to "Television Engineering Handbook," edited by K. Blair Benson, McGraw-Hill (1986), which is incorporated herein by reference.

The patient's tooth shade information is typically communicated to a laboratory which manufactures the reconstructed tooth via a plurality of porcelain coatings. This process of constructing porcelain layers onto a tooth model is known in the art; although the specification of the differing porcelain layers by data generated by an intraoral camera is specific to the invention. In the event that certain fractions of different porcelain layers are needed, such as described above, the system of the invention again provides and generates the appropriate shade fractions corresponding to the multiple layers.

Other color theory details, including the adding and subtracting of multiple colors, may be found with reference to the following patents, each of which is expressly incorporated herein by reference: U.S. Pat. No. 5,383,020, entitled "Method and apparatus for determining the color of a translucent object such as a tooth;" WO 86/03292, entitled "A spectrum-photometer device for exactly determining the color of a dental plate and or dental pluggings;" U.S. Pat. No. 3,986,777 entitled "Tristimulus calorimeter for use in the fabrication of artificial teeth;" U.S. Pat. No. 4,654,794 entitled "Methods for determining the proper coloring for a tooth replica;" U.S. Pat. No. 4,836,674 entitled "Method and apparatus for determining color, in particular of a dental prosthesis;" U.S. Pat. No. 5,231,472 entitled "Color matching and characterization of surface coatings;" and U.S. Pat. No. 4,247,202 entitled "Automatic computing color meter."

Figure 8:
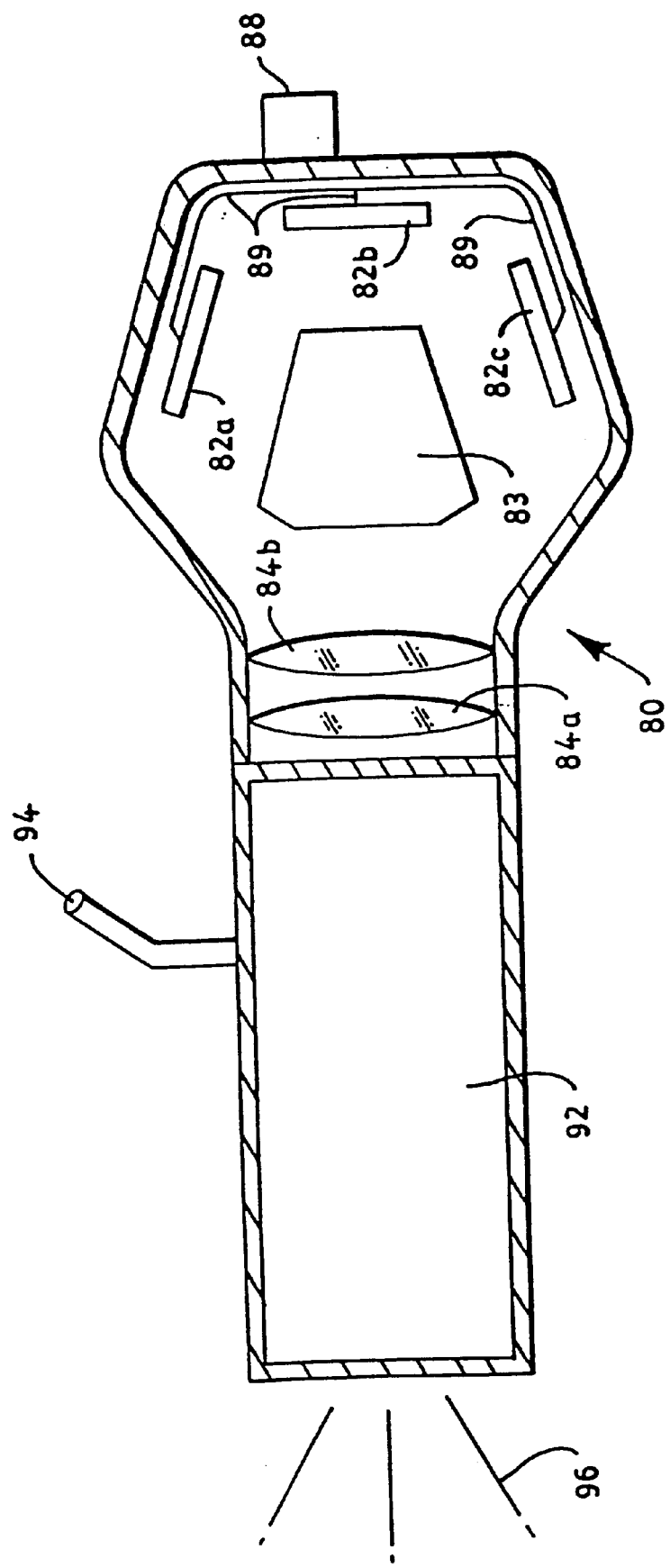
FIG. 8 illustrates a common aperature color CCD camera and handpiece constructed according to the invention, and which form another embodiment of a shade analyzer system.

FIG. 8 illustrates another embodiment of the invention, and which includes a common aperature color CCD camera 80. The camera 80 is commonly known as a "threechip" color camera because of the three separate area CCD arrays (and preamplifiers) 82a, 82b, 82c. A complex prism 83 slits the light energy entering through the aperture lenses 84a, 84b into the three RGB color components. That is, each of the arrays 82 uniquely corresponds to one of the three color spectrums, such as Red. A housing 86 surrounds and protects the camera 80 from contact with external influences. The outputs from the three arrays 82a, 82b, 82c connect to a common RS232 interface 88, which is in turn connected, via signal lines 89, to a digital video processor shade analyzer subsystem, such as described above.

The size of the camera 80 is small, typically about 40 mm$^3$ or less. One manufacturer of a camera 80 includes Richter Enterprises, of Del Norte, Colo., which makes the Model AD01 Common Aperture Camera.

The front aperture section 90 of the camera 80 connects to a handpiece 92—similar to the handpieces 32a, 32b described above—which is utilized by the dentist to illuminate and capture light imagery within the patient's mouth. For example, one acceptable handpiece 92 is an endoscopic handpiece which derives illumination from an external source 94, e.g., a lamp. The source is imaged through the endoscope to provide illumination 96 at the target area designated by the dentist; and the endoscope recaptures the light scattered from within the patient's mouth to form an image, in conjunction with the camera 80, at the several CCD arrays 82a, 82b, 82c.

Each of the CCDs 82a, 82b, 82c is coaligned with the other so that three distinct pixels, i.e., one each corresponding to R, G or B chromaticities, substantially view the same target point. Typically, each of the pixels specifies an 8-bit (or even 10-bit) color, so that, in total, the combination of the three arrays form a possible 256×256×256 colors. This provides sufficient resolution to discern several shades of white within the shade guides, so that a particular guide may be matched with a patient's tooth.

Figure 9:
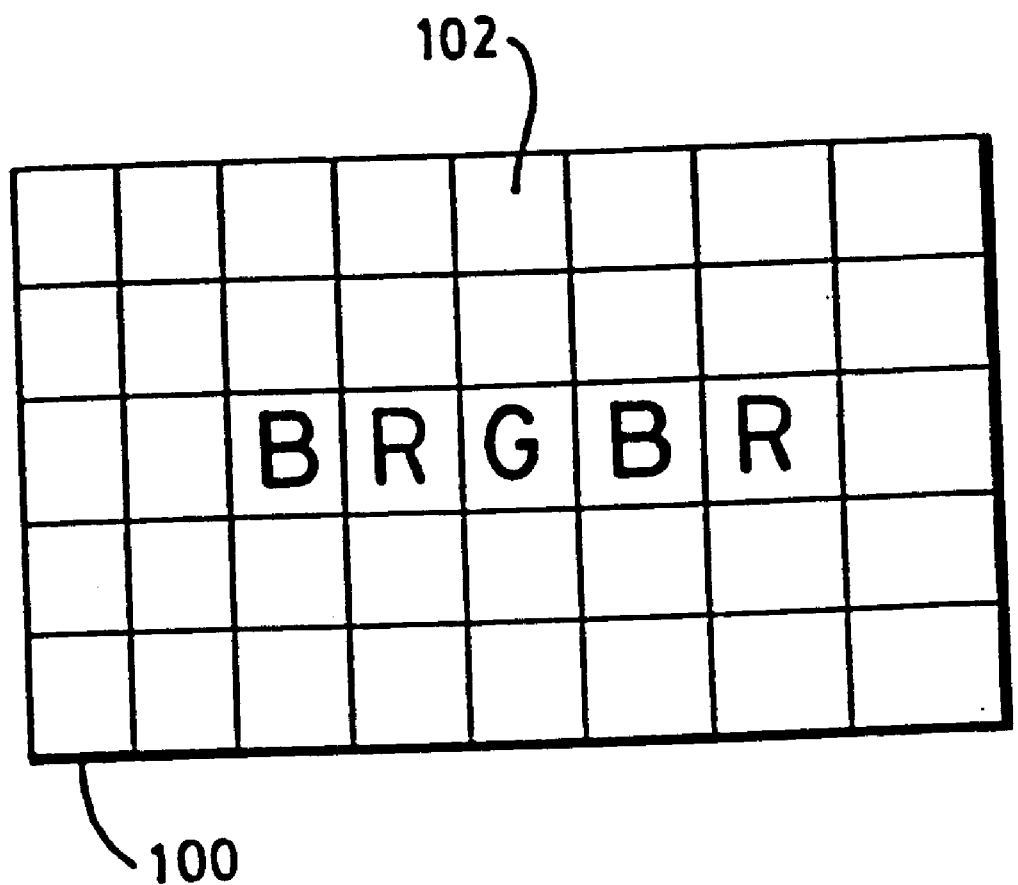
FIG. 9 shows an alternative CCD array technology, according to the invention, and which is suitable for use within the camera of FIG. 8.

Alternatively, the arrays of FIG. 8 can be replaced with a single array 100, FIG. 9 (as such, the prism 83 is also no longer required). Such an array 100 is popular in lower cost Camcorder technologies. In one embodiment, the array 100 has serial RGB pixels along each two of the array, here denoted as "R", "G" and "B" within each pixel 102. This scheme reduces resolution; although it also reduces costs. As above, each of the three RGB pixels is utilized to assess and determine shade color.

EXAMPLE

The following example illustrates the use of a CCD camera to provide a dental color match for a patient's tooth. The camera was connected to a Personal Computer ("PC"). Several images of the patient's tooth were taken and compared for consistency and definition of color variance. To verify consistency, a software program was used to interface with the camera to take snapshot images of Vita Limun Vacuum Shades using the camera. The images were be stored on the PC for later analysis. All images included the sample media and color reference at the same location in the frame. A software program was written to analyze the stored snapshots. Evaluation areas (sample and reference) were sampled and results of the color analysis were presented. The color reference was used to overcome the auto-brightness which could not be disabled on the camera. The software automatically adjusted the sample results using the color reference.

The following camera was used and found to be preferred:
Type: Intraoral
Manufacturer: Welch-Allyn
DLS 400 Light source (Sn: D97-652920)
DHP Hand Piece
Lenses Green (General purpose), White (Close Focus) and Red (Full Face)

This camera has a built in light source with a color temperature of 5600K and was select to provide more consistent results than using a separate light source. The camera has auto white balance that is turned off when using the light source. The camera has no external control of auto-brightness, but it is controllable by the camera firmware.

An Image Acquisition Hardware (Frame Grabber) that was used was an Alaris Quick Video Transport. This results in a sampled color of 24 bits being stored on the PC. It has an S-Video (SVHS) input to match the output from the camera to provide the best possible results by using the best signal output from the camera.

The software uses a Twain protocol interface to grab images from the camera using the Frame Grabber. This is a standard software interface that allow other cameras and Frame Grabbers to be tested without the need for a change of software.

The camera was used to provide an image of the sample area of a patient's tooth on a monitor screen. The PC and frame grabber captured the image onto the hard disk for analysis. The images stored from the Frame Grabber were selected to be 640 pixels wide by 480 pixels high, using 24 bits per pixel for color, with 8 bits each for red, green and blue ("RGB"). The color is coded as red, green and blue signals, each with a value from 0 to 255. An RGB value of (0,0,0) represents black, and (255,255,255) represents white.

As the RGB values alone are not very intuitive for analyzing color, they were converted into the Hue Saturation and Intensity color space by using an algorithm. The Gonzalez and Woods method is used to calculate Hue Saturation and Intensity (HSI), as follows:

R=Red value for pixel
G=Green value for pixel
B=Blue value for pixel
Intensity=⅓(R+G+B)
Saturation=1−(3/R+G+B))*Min(R, G, B)
Hue=Cos$^{-1}$((0.5*((R−G)+(R−B)))/((R−B)*(G−B))$^{0.5}$)
If S=0, Hue is meaningless
If B3/Intensity)>(G/Intensity) then Hue=360−Hue
Since Hue is an angle in degrees values were normalized to 0.1 with Hue=Hue/360

The RGB color space is a simple cube, with R, G and B emanating from one corner along three perpendicular edges. The origin corner (0,0,0) is black, and the opposite corner (1,1,1) is white. All points along this line from corner to corner are shades of grey. The HSI color space is this same cube stood on the origin corner, with the Black White line being vertical. The black-white line is the intensity axis, the hue is given by an angle from the intensity axis and the saturation is the distance from the intensity axis to the color point (i.e., the radius). The new VITAPAN 3D-Master Shade system uses an L*a*b* Color Sphere to determine tooth shades based on Value, Chroma and Hue. It is possible to convert the RGB values to this color system, if necessary or desired.

The software for analyzing the image was written to allow the selection of a particular area of the tooth for analysis. This area was actually selected by human eye, and was a matter of judgement.

The initial tests using a normal video camera and desktop computer camera showed that the white color balance used by these cameras (and auto brightness) changed the colors of the subject viewed by the cameras even while trying to maintain constant conditions. On most cameras it is not possible to turn off the auto white balance.

The initial tests with the Welch-Allyn intraoral camera were performed by using the camera hand held, as this reproduces the current method used by a dentist to take such pictures. These test gave pictures of varying quality, orientation, distance from tooth etc. The comparison of the data taken from these pictures indicated that the camera can determine color differences, but that the auto brightness on the camera could cause problems.

A3, B3 and C3 Vita Shade Images were imaged by the hand held camera. The shades were still in their holder, and the camera passed over each one to capture the images. The software program was used to sample the images, but it was found that intensity values across the different sample sets varied greatly. The lighter shades (A1, B1, C1, and D2) gave the poorest cross sample correlation, possibly due to the sample color being closer to white with ambient lighting and reflection causing interferences.

Figure 10:
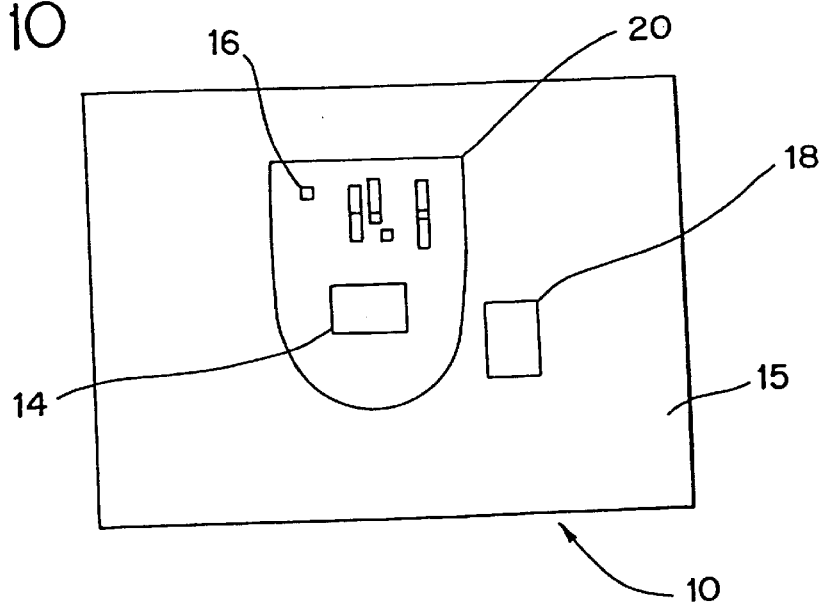
FIG. 10 is a perspective view of a background color reference member.

The inclusion of a reference color around the sample helped to give a reference for intensity correction, but the varying lens distance from sample still gave images of varying quality. The use of a reference color was an attempt to simultaneously obtain distance measurement, color reference and stray light protection. As shown in FIG. 10, a background color reference member 10 was a strip of construction paper 15 with a cut-out or opening 20 that approximates the shape of the patient's tooth or a reference such as a Vita shade. Each image was taken at approximately the same distance and orientation. Better results were obtained than without the reference, but there was still a problem with the Hue, and the varying distance of the camera, and hence light source from the sample. Varying angle on the reference also made differences. When measuring the color of the tooth or reference shade, the sampled area 14 should be chosen to avoid lamp reflections 16 or other inconsistencies. The background 18 of the reference member is also sampled.

The final preferred method used a single fixed area of the image for sample and a separate area for reference, with the image size and orientation controlled by the use of a sample box or isolation sleeve. A cream color was chosen for the sleeve as it could also be used as the reference color for all tests. The isolation sleeve was attached firmly to the camera head to allow the light source to illuminate the inside of the sleeve and to enable the camera lens to have an unobstructed view of the bottom inside face of the sleeve and the sample opening.

Figure 12:
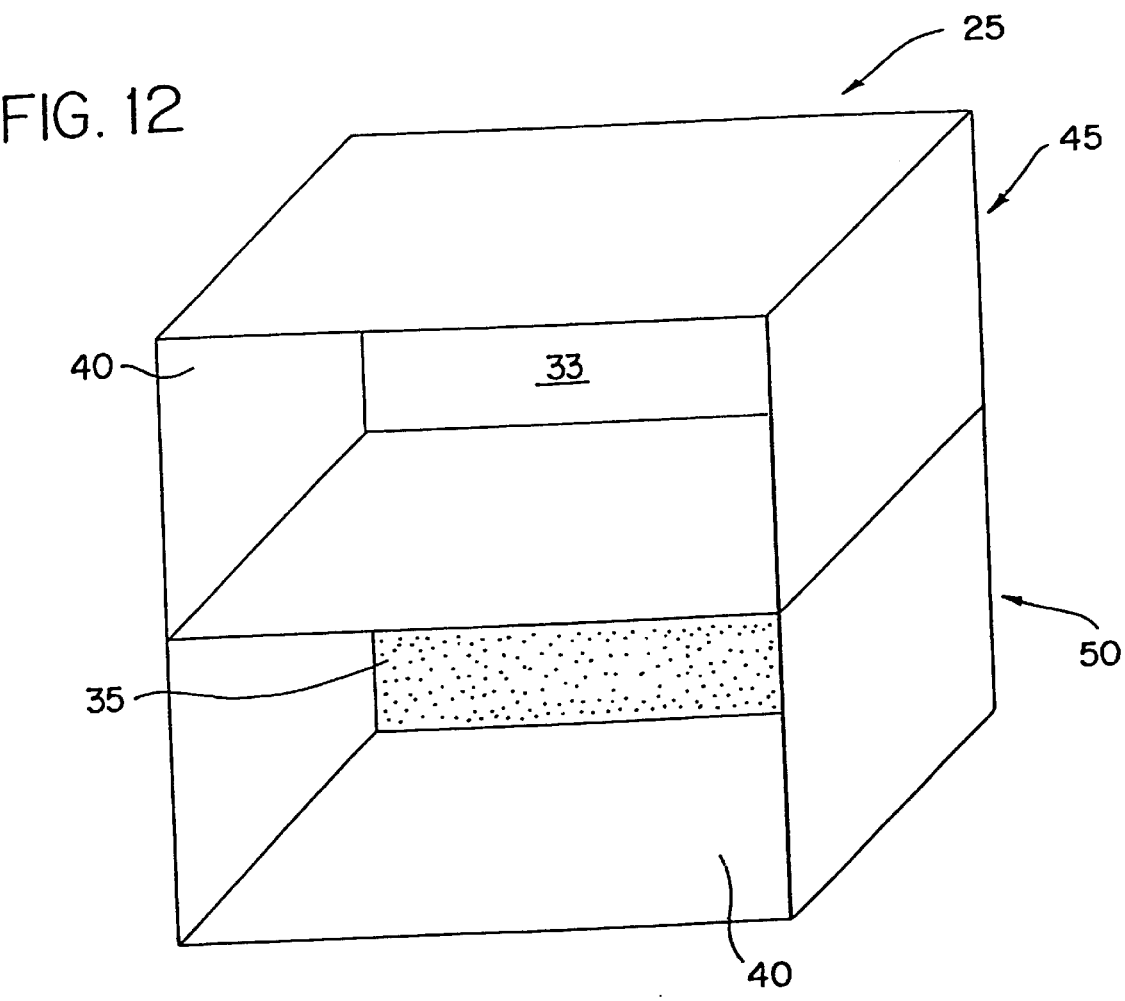
FIG. 12 is a perspective view of the isolation sleeve of FIG. 11 viewed from the camera when detached therefrom.
Figure 11:
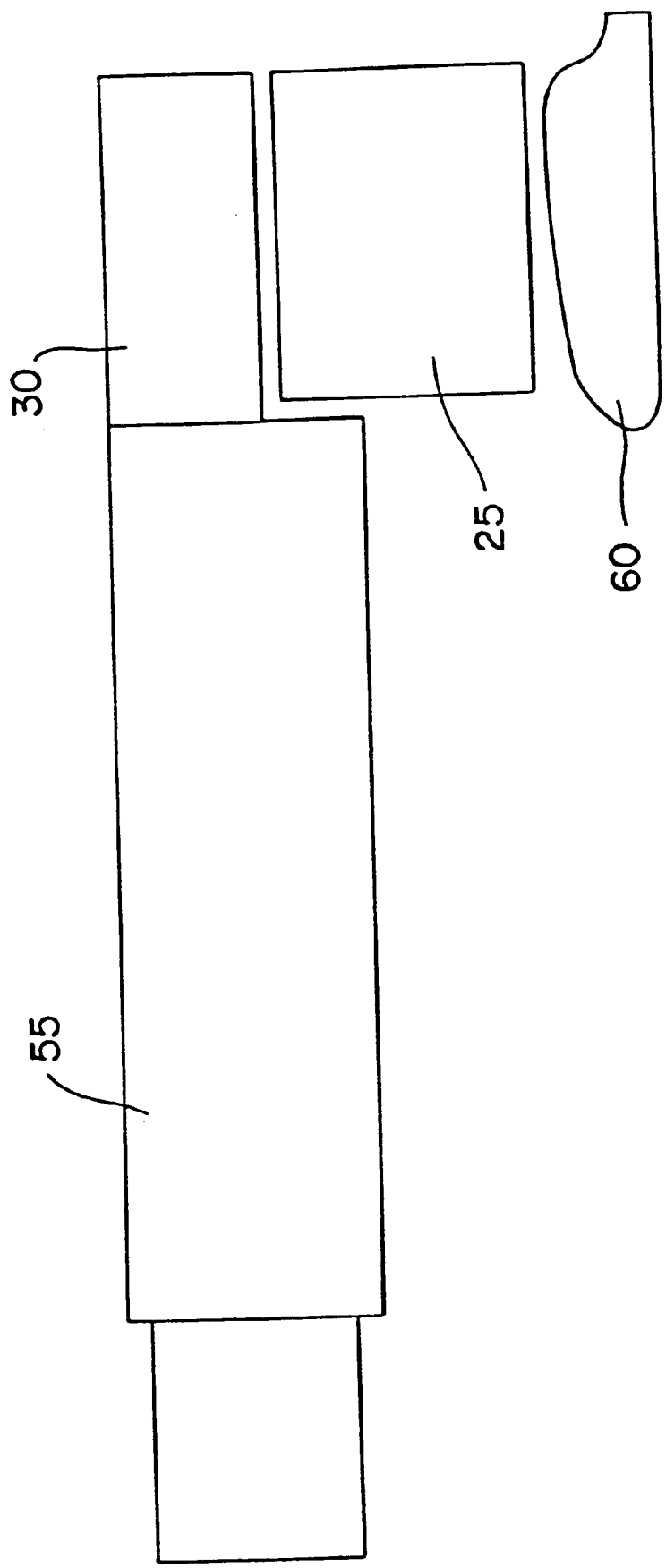
FIG. 11 is a side schematic view of a camera and isolation sleeve according to the invention.

As shown in FIG. 11, the isolation sleeve 25 surrounds the camera lens 30, and has an opening 33 in the end opposite to the lens to accommodate the Vita shade or the patient's tooth 60 to be sampled. The isolation sleeve 25 reduced two major consistency problems encountered when using the camera without it. Firstly, it reduced the variation in distance and orientation of the camera 55 from the subject, and secondly, it removed unwanted ambient light contamination. As shown in FIG. 12, the inside surfaces 40 of the isolation sleeve 25 were made matt black to avoid reflection and prevent color contamination of the subject. The color reference 35 was provided in a separate chamber in the box to prevent cross color contamination with the tooth or sample shade. A double isolation sleeve 25 was used with both chambers 45, 50 in front of the light source and camera lens, but with the subject and the color reference in separate chambers. Half of the resultant image was the color reference, while the other half was of the tooth to be evaluated.

Only one area was sampled on the subject tooth, although it is preferable to divide the subject into multiple target areas, and construct a shade database for each sub-section. Thus, when a patient's tooth color partially matches two shades, the areas can be referenced individually.

Where the sample area contains a reflection of the light source, this greatly affects the averaged values for the colors. The lamp reflection is usually samples as very near bright white (255,255,255)). To help omit these points and any dark spots on the sample, a selective pixel usage was adopted. The area being sampled was averaged, and the Maximum and Minimum RGB values noted. The area was then rescanned and any pixel with any of the RGB values outside of half way from the Average to Max value or Average to Min value are ignored, i.e.:

$$(Min+Average)/2 < Valid\ Value < (Max+Average)/2$$

When the color references were compared, it was found that as different shades were viewed, the saturation, intensity and hue of the reference also changed. This was most likely due to reflection from the sample contaminating the color reference, and the fact that the camera automatically adjusted for brightness. Hence the greatest change is seen in intensity and saturation.

The values for the color reference were used to adjust the values taken from the sample in the same image. The difference in the value from the color reference for each picture was lineally adjusted by a delta value such that the adjusted values were then identical for each image. This delta value for each image was also applied to the values taken for the sample. This made the comparison of one image to another much more consistent. The hue variation in the reference sample was found to be less than 1.5% of the camera's full range.

While the intensity comparison of the samples exhibited a variation in the shades, there is still variation in the levels from one set of samples to another i.e., the different images of the sample shade give different results. Although the saturation varied over a larger range of values, the difference between the sample sets for the same shade was still noticeable.

The hue of the sample taken from the images was erratic and showed very poor correlation between the same shade in the different sets of samples. To make the images more consistent, the image is adjusted by applying a delta to the sampled RGB value that would make the reference color become the same value for each image. This compensates for the auto brightness control of the camera. When the reference adjustments were taken into account, the correlation of the results improved. The RGB reference values were set to R: 0.66583, G: 0.57465, and B: 0.55137. A reflection filter was also inserted into the sampling algorithm. This attempts to ignore any pixel that is more than 50% away from the average value. The correlation between sample sets improved with these adjustments, and with reflection filtering.

The results showed that the use of a normal CCD camera with an external light source is possible, but would require a more extensive calibration system than is required by using an internal light source. The color temperature of the light being seen by the camera would vary depending on the location of the patient near the light source, amount of sunlight experienced on the day, and on the type of room lighting used. Fluorescent lighting gives a flickering light, which can cause problems with certain shutter speeds on the camera.

The camera must also be able to deselect the auto white balance which would distort colors in favor of a balanced picture, and if possible the auto brightness control which would change intensity. This would give rise to much manual adjustment as the ambient lighting conditions change to ensure the camera was operating non-saturated.

An intraoral camera with a built in light source that is delivered to the sample from the camera head is therefore preferred. The first observation from using the camera was the inaccuracy and poor repeatability of trying to sample a shade using the camera held in the hand only. The distance from the sample seems to be critical, and the ambient light contaminating the sample caused poor readings. Therefore, it is preferred that the ambient light be prevented from contaminating the sample, and that a distance reference from the camera lens to the sample be provided. The initial trial with the sample box attached to the camera head resolved these problems and provided good results.

It is useful to avoid the introduction of stray light as the color reference is affected by color contamination from light reflected from the sample. When the color reference values were used to create a correction factor for the RGB values obtained from the sample, the isolation sleeve 25 minimizes these problems by reducing the light reflected from the sample and the light contamination of the color reference.

The isolation sleeve 25 is attached to the camera head to prevent stray light from entering. The sleeve is shown viewed from the camera side. The orientation is dependent on the light source, as it is preferred to have the light distributed evenly into both chambers of the sleeve. The black walls of the isolation sleeve can cause interferences with the auto brightness control of the camera, as the auto brightness control will try to maintain an 'average' brightness for the whole image and thus may cause the actual sample or color reference to saturate. This is where the camera auto adjusts to the point that the sample returns a color value of pure white to balance the black in the rest of the image, and all shades of the white, and thus the real color will be lost. The auto brightness should be turned off for best results.

The color reference in the isolation sleeve can be made consistently, so that no further calibration should be required. Each image will calibrate itself. If the color reference is not sufficiently consistent, the reference itself will need calibration using a further color reference (a Vita shade for example). If the reference fades with use, it can be replaced to insure reference consistency.

If the Colour Space of the Lumin Vacuum Shade Guide is not evenly distributed, the current system of first selecting the hue, and then the saturation and lightness makes the analysis for the software difficult if the camera cannot accurately determine the exact hue. The camera is being used to determine hue differences over a very small range of its operative area (less than 1.5% of the full camera range). The resolution required to perform this analysis should be available on the camera, and discernible on the PC. As this is a relatively small range of values, the repeatability of the image taking process must be made very high. It is not just a case of taking a picture of the tooth and analyzing it. The conditions required by the camera must be stabilized. Again, the isolation sleeve provides a controlled environment such that repeatable and reproducible images are obtained. The images contain the color reference, and can if necessary be sent to the laboratory together with the dentist's requirements for reconstructing the tooth. For infection control, the isolation sleeve should be made to be disposable.

Older shade guides are not evenly spaced and this can introduce inconsistencies in the results. Newer 3D color shades are more evenly distributed and thus make color differentiation easier for the camera. The new shades include 5 numbered lightness (value) categories. These are then subdivided into a choice of three Chroma levels (1, 2, or 3) and for lightness groups 2, 3 and 4 there are three hues (L, M and R). This requires a different approach to analyzing the sampled data, as priority is now given to the Lightness value (Intensity) and then the Chroma (Saturation). It was found that both values gave good correlation across different data sets. The Hue is then only divided into three possible categories (depending on the lightness category) which makes the color analysis much more consistent. The sample box also provides better color and hue correction as well as intensity correction for these new shades.

Further details of these tests can be found in the report that is annexed to U.S. Pat. No. 5,9961,324. It should be apparent to those skilled in the art that certain modifications can be made to the invention herein without departing from the true scope of the invention.

What is claimed is:

1. A method for determining a patient's tooth shade, which comprises:
   generating an image of a patient's tooth wherein the image includes color information representative of the patient's tooth shade;
   storing color information representative of a plurality of tooth shades; and
   comparing the color information of the image with the stored tooth shade color information to identify one or more tooth shades having a combined color that corresponds to the patient's tooth shade.

2. The method of claim 1 wherein the image of the patient's tooth and the stored tooth shade color information are electronically displayed in color to enable a viewer to comparatively determine the color of the patient's tooth shade.

3. The method of claim 2 wherein the patient's tooth shade is determined by selecting portions of the electronically displayed image of the tooth; determining the color of the selected portions; and comparing that color information with the stored tooth shade color information to determine the color of that portion of the patient's tooth.

4. The method of claim 3 wherein the selection of portions of the tooth is repeated until a tooth shade color is determined for all spatial locations of the image of the patient's tooth.

5. The method of claim 4 wherein the patient's tooth shade is determined by averaging the color information at selected portions of the image before comparing the averaged color information with the stored tooth shade color information.

6. The method of claim 1 which further comprises utilizing a camera that includes a lens to obtain the image of the patient's tooth, providing the camera lens with an unobstructed view of the patient's tooth, illuminating the patient's tooth in order to generate the image, and isolating the patient's tooth from light from external sources to prevent such light from interfering with the generation of the image while positioning the camera lens at a reproducible distance from the patient's tooth.

7. The method of claim 6 which further comprises providing a reference color adjacent the tooth for intensity correction of the color information.

8. The method of claim 6 wherein the camera used to obtain the image of the patient's tooth is a digital camera color information representative of the tooth shades is obtained from the same digital camera and is stored electronically before the patient's tooth is imaged.

9. The method of claim 1 which further comprises electronically forwarding the patient's tooth shade color(s) to a dental laboratory for use in reconstruction of a tooth for the patient.

10. The method of claim 9 wherein the laboratory manufactures the reconstructed tooth utilizing a plurality of porcelain coatings.

11. The method of claim 1, which further comprises utilizing a camera that includes a lens to obtain the image of the patient's tooth, providing the camera lens with an unobstructed view of the patient's tooth, illuminating the patient's tooth in order to generate the image, and positioning the camera lens to control image size and orientation.

12. A system for determining the tooth shade of a patient's tooth, comprising:
   a camera having a lens for capturing an image of a patient's tooth, the image including color information representative of a color of the tooth, an isolation sleeve surrounding at least the camera lens to prevent light from external sources from interfering with capturing the image of the patient's tooth and having an opening opposite the lens to accommodate the patient's tooth to be imaged, a light source for illuminating the patient's tooth through the isolation sleeve, and a shade analyzer sub-system connected for electrical communication with the camera, the shade analyzer having
  (i) color processing means for determining the color of the patient's tooth from the color information of the image,
  (ii) storage means for storing shade information representative of a plurality of tooth shades, each of the tooth shades corresponding to a different tooth color,
  (iii) color correlation means for comparing the color of the patient's tooth to the plurality of tooth shades and for identifying a tooth shade with a color corresponding to the color of the patient's tooth, and
  (iv) means for communicating the identified tooth shade to a user of the system.

13. The system of claim 12, wherein the isolation sleeve has an open interior that enables the camera lens to have an unobstructed view of the patient's tooth, and that assists in positioning the camera lens at a reproducible distance from the patient's tooth, wherein the light source illuminates the interior of the isolation sleeve and the patient's tooth.

14. The system of claim 12, wherein the isolation sleeve is firmly attached to the camera and includes a color on its inside surface to reduce or prevent color contamination of the patient's tooth.

15. The system of claim 12, wherein the isolation sleeve includes a reference color near the patient's tooth to assist in evaluation the color of the patient's tooth.

16. The system of claim 15, wherein the reference color is provided in a separate chamber from that used to view the patient's tooth.

17. The system of claim 12, wherein the storage means is a computer hard disk or floppy disk storage medium that includes digital color images of the plurality of tooth shades.

18. The system of claim 12, wherein the camera is a color CCD camera comprising a single CCD array, the array including a plurality of proximately located pixels corresponding to a color chromaticity selected from the group of red, green and blue, each of any group of three pixels having a different color associated therewith.

19. The system of claim 12, wherein the isolation sleeve also provides control of image size and orientation.

* * * * *

UNITED STATES PATENT AND TRADEMARK OFFICE
CERTIFICATE OF CORRECTION

PATENT NO.   : 6,561,800 B2
DATED          : May 13, 2003
INVENTOR(S) : Lehmann et al.

It is certified that error appears in the above-identified patent and that said Letters Patent is hereby corrected as shown below:

<u>Title page,</u>
Item [56], References Cited, U.S. PATENT DOCUMENTS, add the following:

| | | | |
|---|---|---|---|
| -- 3,861,044 | 01/1975 | Swinson, Jr. | 32/17 |
| 3,975,760 | 08/1976 | Yamanaka et al. | 358/41 |
| 3,986,777 | 10/1976 | Roll | 356/176 |
| 4,016,598 | 04/1977 | Yamanaka | 358/41 |
| 4,106,056 | 08/1978 | Nagumo et al. | 358/56 |
| 4,247,202 | 01/1981 | Failes | 364/310 |
| 4,414,635 | 11/1983 | Gast et al. | 356/526 |
| 4,518,258 | 05/1985 | Broersma | 364/405 |
| 4,547,074 | 10/1985 | Hinoda et al. | 364/405 |
| 4,575,805 | 03/1986 | Moermann et al. | 364/474 |
| 4,591,900 | 05/1986 | Heeb et al. | 358/44 |
| 4,616,933 | 10/1986 | Leveque et al. | 356/416 |
| 4,623,973 | 11/1986 | Hoffrichter et al. | 364/405 |
| 4,654,794 | 03/1987 | O'Brien | 364/413 |
| 4,692,481 | 09/1997 | Kelly | 523/210 |
| 4,836,674 | 06/1989 | Leguime et al. | 356/319 |
| 4,881,811 | 11/1989 | O'Brien | 356/323 |
| 4,903,122 | 02/1990 | Ozaki et al. | 358/48 |
| 4,919,617 | 04/1990 | Antons et al. | 433/26 |
| 4,978,296 | 12/1990 | Anton et al. | 433/26 |
| 5,012,431 | 04/1991 | Stanziola | 364/526 |
| 5,124,797 | 06/1992 | Williams et al. | 358/225 |
| 5,231,472 | 07/1993 | Marcus et al. | 356/402 |
| 5,240,214 | 08/1993 | Thompson | 433/26 |
| 5,273,429 | 12/1993 | Rekow et al. | 433/215 |
| 5,282,025 | 01/1994 | Sato | 358/44 |
| 5,313,267 | 05/1994 | MacFarlane et al. | 356/405 |
| 5,340,309 | 08/1994 | Robertson | 433/69 |
| 5,373,364 | 12/1994 | Krzyminski | 356/323 |
| 5,383,020 | 01/1995 | Vieillefosse | 356/405 |
| 5,430,811 | 07/1995 | Fukushima et al. | 382/254 |
| 5,431,562 | 07/1995 | Andreiko et al. | 433/25 |
| 5,452,219 | 09/1995 | Dehoff et al. | 364/474.05 |
| 5,453,009 | 09/1995 | Feldman | 433/215 |
| 5,498,157 | 03/1996 | Hall | 433/26 |
| 5,549,476 | 08/1996 | Stern | 433/233 |
| 5,587,912 | 12/1996 | Andersson et al. | 433/215 |
| 5,685,712 | 11/1997 | Fischer | 433/26 |
| 5,690,486 | 11/1997 | Zigelbaum | 433/29 |
| 5,692,900 | 12/1997 | Fischer | 433/26 |
| 5,725,372 | 03/1998 | Leon | 433/26 |
| 5,745,229 | 04/1998 | Jung et al. | 356/73 |
| 5,733,126 | 03/1998 | Andersson et al. | 433/233 |
| 5,759,030 | 06/1998 | Jung et al. | 433/29 |
| 5,798,839 | 08/1998 | Berner et al. | 356/402 |
| 5,823,778 | 10/1998 | Schmitt et al. | 433/214 |
| 5,851,113 | 12/1998 | Jung et al. | 433/29 |
| 5,851,115 | 12/1998 | Carlsson et al. | 433/215 |
| 5,871,351 | 02/1999 | Jung et al. | 433/29 |
| 5,880,826 | 03/1999 | Jung et al. | 356/73 |
| 5,938,446 | 08/1999 | Andersson et al. | 433/25 |
| 6,008,905 | 12/1999 | Breton et al. | 356/402 |
| 6,030,209 | 02/2000 | Panzera et al. | 433/26 |
| 6,038,024 | 03/2000 | Berner | 356/326 |
| 6,111,650 | 08/2000 | Rawicz et al. | 56/402 |
| 6,244,863 | 06/2001 | Rawicz et al. | 433/26 -- |

UNITED STATES PATENT AND TRADEMARK OFFICE
CERTIFICATE OF CORRECTION

PATENT NO. : 6,561,800 B2
DATED : May 13, 2003
INVENTOR(S) : Lehmann et al.

It is certified that error appears in the above-identified patent and that said Letters Patent is hereby corrected as shown below:

<u>Title page (cont'd),</u>
After the listing of "U.S. PATENT DOCUMENTS", insert the following:

-- FOREIGN PATENT DOCUMENTS

| EP | 360657   | 03/1990 |
|----|----------|---------|
| JP | 4301530  | 10/1992 |
| JP | 4338465  | 11/1992 |
| WO | 86/03292 | 06/1986 |
| WO | 91/02955 | 03/1991 |
| WO | 95/15731 | 06/1995 -- |

Signed and Sealed this

Ninth Day of September, 2003

JAMES E. ROGAN
*Director of the United States Patent and Trademark Office*